United States Patent
Spenciner et al.

(10) Patent No.: US 12,193,657 B2
(45) Date of Patent: *Jan. 14, 2025

(54) SELF-ASSEMBLING SUTURE ANCHOR ASSEMBLY, SURGICAL KIT, AND SURGICAL REPAIR METHOD

(71) Applicant: Medos International Sarl, Le Locle (CH)

(72) Inventors: David B. Spenciner, North Attleboro, MA (US); Benjamin Chan, Naples, FL (US)

(73) Assignee: Medos International Sarl, Le Locle (CH)

(*) Notice: Subject to any disclaimer, the term of this patent is extended or adjusted under 35 U.S.C. 154(b) by 478 days.

This patent is subject to a terminal disclaimer.

(21) Appl. No.: 17/568,331

(22) Filed: Jan. 4, 2022

(65) Prior Publication Data

US 2022/0125424 A1    Apr. 28, 2022

Related U.S. Application Data

(60) Continuation of application No. 16/374,377, filed on Apr. 3, 2019, now Pat. No. 11,241,224, which is a
(Continued)

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0409* (2013.01);
(Continued)

(58) Field of Classification Search
CPC .......... A61B 17/0401; A61B 17/06116; A61B 2017/0409; A61B 2017/0414;
(Continued)

(56) References Cited

U.S. PATENT DOCUMENTS 5,324,308 A    6/1994    Pierce
5,405,359 A    4/1995    Pierce
(Continued)

OTHER PUBLICATIONS

U.S. Appl. No. 14/037,735, filed Sep. 26, 2013, Self-Assembling Suture Anchor Assembly, Surgical Kit, and Surgical Repair Method.
(Continued)

*Primary Examiner* — Sarah W Aleman
*Assistant Examiner* — Mikail A Mannan
(74) *Attorney, Agent, or Firm* — Mintz Levin Cohn Ferris Glovsky and Popeo, P.C.

(57) ABSTRACT

A suture anchor assembly includes a main suture strand, a plurality of suture arms, and a plurality of suture anchor elements connected to the main suture strand by a suture arm. The suture anchor elements are configured to rest against a cortex of a bone to provide an anchor when they are in a deployed configuration. The suture anchor assemblies can be employed in place of or in addition to traditional suture anchors. The assemblies, kits, and methods described herein can be utilized in a variety of procedures and locations in the body where anchoring a graft or tissue adjacent a bone is desired, including, for example, rotator cuff repair and ligament (e.g., the anterior cruciate ligament or ACL) reconstruction and/or repair.

20 Claims, 5 Drawing Sheets

Related U.S. Application Data division of application No. 14/037,735, filed on Sep. 26, 2013, now Pat. No. 10,285,684.

(52) U.S. Cl.
CPC ............... *A61B 2017/0414* (2013.01); *A61B 2017/0417* (2013.01); *A61B 2017/0458* (2013.01)

(58) Field of Classification Search
CPC .... A61B 2017/0458; A61B 2017/0417; A61B 2017/0445; A61B 2017/0464; A61B 2017/0404; A61B 2017/0475; A61F 2002/0876; A61F 2002/0882; A61F 2002/0888; A61F 2/0811
See application file for complete search history.

(56) References Cited

U.S. PATENT DOCUMENTS

| | | |
|---|---|---|
| 5,690,678 A | 11/1997 | Johnson |
| 6,056,773 A | 5/2000 | Bonutti |
| 6,071,292 A | 6/2000 | Makower et al. |
| 6,156,039 A | 12/2000 | Thal |
| 6,287,325 B1 | 9/2001 | Bonutti |
| 7,494,496 B2 | 2/2009 | Swain et al. |
| 7,658,750 B2 | 2/2010 | Li |
| 7,686,838 B2 * | 3/2010 | Wolf ............... A61B 17/0401 606/325 |
| 10,285,684 B2 | 5/2019 | Spenciner et al. |
| 11,241,224 B2 | 2/2022 | Spenciner et al. |
| 2005/0187577 A1 | 8/2005 | Selvitelli et al. |
| 2005/0228448 A1 * | 10/2005 | Li ..................... A61B 17/0401 606/232 |
| 2005/0251209 A1 | 11/2005 | Saadat et al. |
| 2008/0103528 A1 | 5/2008 | Zirps et al. |
| 2010/0076497 A1 | 3/2010 | Zwirkoski |
| 2010/0121376 A1 | 5/2010 | Li |
| 2012/0165866 A1 | 6/2012 | Kaiser et al. |
| 2013/0131809 A1 | 5/2013 | Michielli |
| 2013/0238023 A1 | 9/2013 | Wales et al. |
| 2019/0223861 A1 | 7/2019 | Spenciner et al. |

OTHER PUBLICATIONS

U.S. Appl. No. 16/374,377, filed Apr. 3, 2019, Self-Assembling Suture Anchor Assembly, Surgical Kit, and Surgical Repair Method.

* cited by examiner

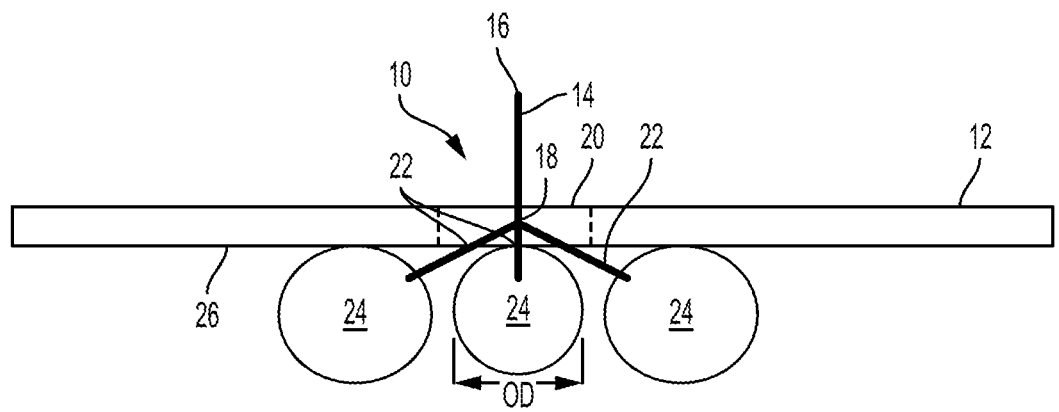
FIG. 1
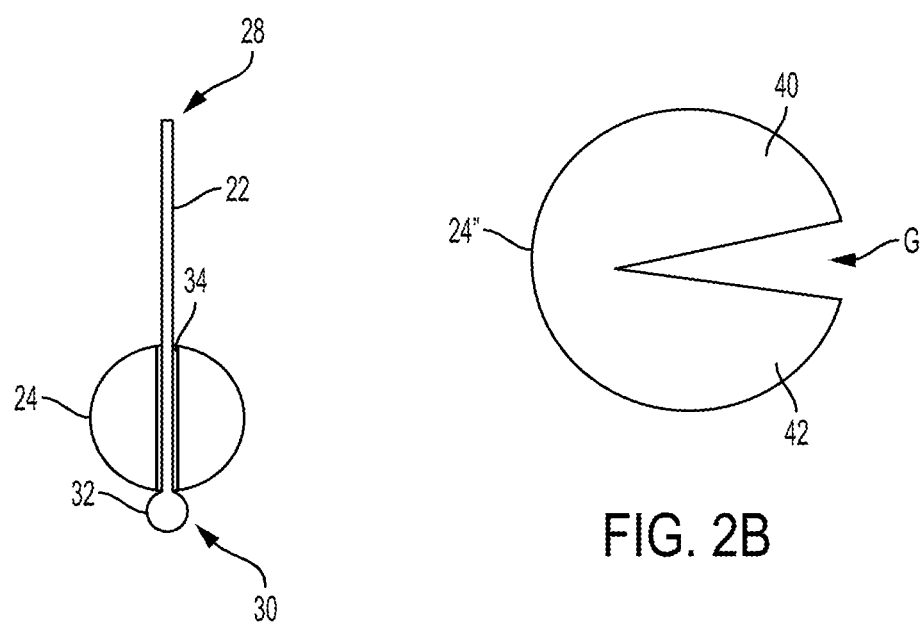
FIG. 2A
FIG. 2B

SELF-ASSEMBLING SUTURE ANCHOR ASSEMBLY, SURGICAL KIT, AND SURGICAL REPAIR METHOD

The present application is a continuation of U.S. patent application Ser. No. 16/374,377 entitled "Self-Assembling Suture Anchor Assembly, Surgical Kit, and Surgical Repair Method" filed Apr. 3, 2019, which is a divisional of U.S. patent application Ser. No. 14/037,735 entitled "Self-Assembling Suture Anchor Assembly, Surgical Kit, and Surgical Repair Method" filed Sep. 26, 2013, which are hereby incorporated by reference in their entireties.

FIELD

The present disclosure relates generally to surgical procedures, and more particularly to suture anchor assemblies, surgical kits, and surgical repair methods.

BACKGROUND

The complete or partial detachment of ligaments, tendons or other soft tissues from their associated bones within the body occurs relatively frequently. For example, the rotator cuff, a group of four muscles that wrap around the shoulder joint to attach the upper arm to the shoulder blade, in part allows the shoulder to move and turn through a wider range than any other joint in the body. Unfortunately, tears of the rotator cuff are common, making many routine activities difficult and painful. Similarly, cruciate ligaments of the knee, e.g., the anterior cruciate ligament, are often completely detached or partially detached from the femur or other associated bone. These types of injuries generally result from excessive stresses being applied to the soft tissues. For example, a tissue detaching injury may occur as the result of a fall, overexertion during a work-related activity, during the course of an athletic event, and/or in association with other situations or physical activities.

A number of surgical techniques exist for reattaching detached tissues and/or completely replacing severely damaged tissues. One such technique involves reattachment of detached tissue using traditional attachment devices such as metal staples, sutures over buttons, cancellous bone screws, and/or other anchor devices. These types of traditional attachment techniques and devices may also be used to attach tendon or ligament substitutes to the desired bone or bones. Traditional anchors often rely on the quality of the cortical or cancellous bone in order to obtain sufficient purchase. However, traditional anchors rely on strong and healthy cortical and cancellous bone to achieve sufficient purchase. As a result of certain diseases or as the age of a patient increases, bone mineral density often decreases and can compromise bone strength. This can provide a challenge when using traditional anchors in such bones.

Accordingly, there is a need for improved suture anchor assemblies, surgical kits, and surgical repair methods.

SUMMARY

Described herein are suture anchor assemblies, surgical kits, and methods of affixing soft tissue to bone using such suture anchor assemblies. The suture anchor assemblies described herein are particularly useful for soft tissue fixation when bone quality is insufficient for traditional suture anchors.

In some embodiments, the suture anchor assembly can include a main suture strand and a plurality of suture arms, each having at least a first end attached to the main suture strand. The suture anchor assembly can further include a plurality of suture anchor elements, each connected to one of the suture arms. Additionally, the suture anchor assembly can have a delivery configuration in which each suture element is substantially aligned along a central axis and able to pass through an opening in bone and a deployed configuration in which the suture anchor elements are oriented in a coplanar manner substantially parallel to a bone surface and unable to pass through the opening in bone.

Additionally, surgical repair methods are disclosed. For example, a surgical repair method can include forming a cavity within bone, the cavity having a cavity diameter. The method can include delivering into the cavity a self-assembling suture anchor assembly in a delivery configuration. The suture anchor assembly can have a main suture strand and a plurality of suture elements each connected to the main suture strand by a suture arm. The method can further include deploying the suture anchor assembly by tensioning the main suture strand such that the suture elements are rearranged into a deployed configuration. In the deployed configuration the suture anchor elements are oriented in a coplanar manner substantially parallel to the bone surface and unable to pass through the cavity. Furthermore, the method can include securing a graft or soft tissue connected to the suture anchor assembly to bone.

Surgical kits containing suture anchor assemblies are also disclosed. For example, a surgical kit for repairing tendon or ligament can include a suture anchor assembly and an inserter tool. The suture anchor assembly can include a main suture strand, a plurality of suture arms, each having at least a first end attached to the main suture strand, and a plurality of suture anchor elements, each connected to one of the suture arms, wherein the suture anchor assembly has a delivery configuration in which each suture element is substantially aligned along a central axis and able to pass through an opening in bone and a deployed configuration in which the suture anchor elements are oriented in a coplanar manner substantially parallel to a bone surface and unable to pass through the opening in bone. The inserter tool can be configured to house the suture anchor assembly and to selectively maintain the suture anchor assembly in the delivery configuration until deployment.

BRIEF DESCRIPTION OF DRAWINGS

This invention will be more fully understood from the following detailed description taken in conjunction with the accompanying drawings, in which:

FIG. 1 is a cross-sectional view of an embodiment of a suture anchor assembly in a deployed configuration;

FIG. 2A is a cross-sectional view of an embodiment of a suture arm and a suture anchor element;

FIG. 2B is a cross-sectional view of an embodiment of a suture anchor element;

DETAILED DESCRIPTION

Figure 3:
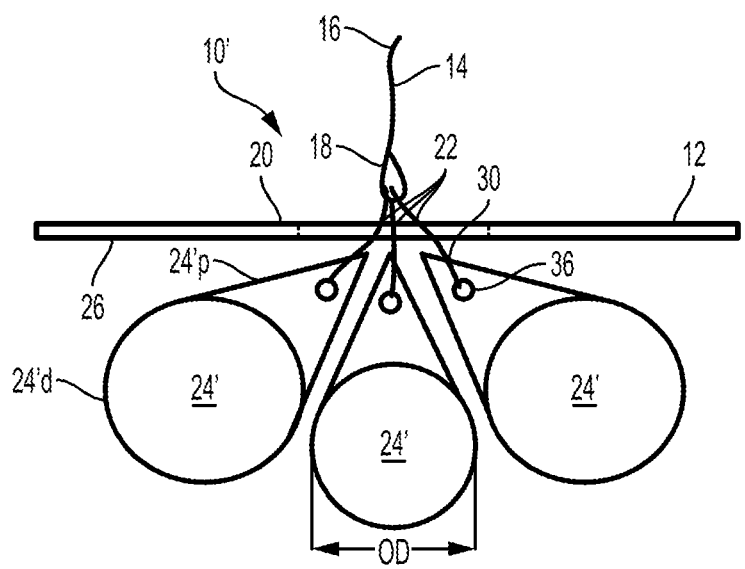
FIG. 3 is a schematic view of an embodiment of a suture anchor assembly in a deployed configuration.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Described herein are suture anchor assemblies, surgical kits, and methods of deploying suture anchor assemblies. In general, suture anchor assemblies described herein include a main suture strand, a plurality of suture arms, and a plurality of suture anchor elements that are configured to rest against a cortex of a bone to provide an anchor when they are in a deployed configuration. The suture anchor assemblies described herein can be employed in place of or in addition to traditional suture anchors, such as buttons, pins, or screws. The assemblies, kits, and methods described herein can be utilized in a variety of procedures and locations in the body where anchoring a graft or tissue adjacent a bone is desired. Numerous procedures in which the suture anchor assemblies described herein can find applicability are well known. Non-limiting exemplary procedures include securing a cruciate ligament (e.g., the anterior cruciate ligament or ACL) graft within a bone tunnel in a patient's femur and rotator cuff repair.

FIG. 1 depicts an embodiment of a suture anchor assembly 10 deployed adjacent a bone 12 to secure soft tissue or a graft (not shown) to bone. The suture anchor assembly 10 can include a main suture strand 14 having a proximal end 16 and a distal end 18 that is configured to extend through an opening 20 in the bone 12. The suture anchor assembly 10 can include a plurality of suture arms 22 with each extending from the main suture strand 14 to one or more of a plurality of suture anchor elements 24. The suture assembly 10 can be configured to have multiple configurations. For example, and as discussed below, the suture assembly can be selectively movable between a delivery configuration and a deployed configuration. In the delivery configuration the suture anchor elements are in an aligned orientation, which allows them to be passed through the opening 20 in bone 12. In the deployed configuration, illustrated in FIG. 1, typically with the aid of a tensile force applied to main suture strand 14, the suture anchor elements are arranged in a coplanar manner substantially parallel to a surface of bone 12 such that the collective suture anchor element arrangement is unable to pass through opening 20. As such, the suture anchor assembly is able to secure soft tissue to bone even when the strength or integrity of bone is compromised and not well suited to the use of traditional suture anchors. In some embodiments, the suture anchor assembly can further include a locking mechanism (not shown) and various other suture strands for use in delivery and deployment of the suture anchor assembly (not shown).

As mentioned, the main suture strand 14 can have a proximal end 16 and a distal end 18. The proximal end of the main suture strand 14 can be configured to be attached to a ligament or tendon graft or to a detached tendon or ligament or replacement tendon or ligament (not shown), thus securing the graft or soft tissue element adjacent to the bone 12, as will be discussed below. The distal end 18 of the main suture strand 14 can be configured to extend through the opening 20 in the bone 12. The distal end 18 can also be configured to allow the suture arms 22 to be attached to the main suture strand 14. For example, the distal end 18 can include a loop or surface feature to tie each suture arm 22 to the main suture strand 14. Alternatively, the distal end 18 of the main suture strand can be configured to have the suture arms 22 integrally formed thereon, for instance by welding, adhering, or otherwise securing the suture arms 22 thereto. In one embodiment, the main suture strand 14 can be formed of a braided suture having a number of filaments (e.g., three). At the distal end 18 of the braided main suture strand, each of the filaments can be separated to form the applicable number of suture arms 22.

The main suture strand 14 can be dimensioned so as to allow sufficient working material for a surgeon, for example by being pliable and long enough to attach the main suture strand 14 to soft tissue or to a graft. The main suture strand 14 can be any length suitable for the various purposes described herein, for example in the range of about 35 cm and 137 cm, and more particularly about 86 cm. The main strand 14 can be any thickness suitable for the various purposes described herein, for example in the range of about #5-0 and #5 as defined by the United States Pharmocopeia ("USP") size designation. More particularly, the main strand 14 can have a thickness of about #2 USP size designation. The main suture strand 14 can be formed of any known suture material, including resorbable, non-resorbable, and/or combinations thereof. Exemplary main suture strand materials include for example, catgut, polyglycolide, and polydioxanone, such as EthiBond® available from Ethicon, Inc. and ORTHOCORD® High Strength Orthopaedic Suture available from DePuy Mitek, Inc. Moreover, the main suture strand 14 can be a monofilament or braided.

As shown in FIGS. 1 and 2A, the suture arms 22 can have a first end 28 and a second end 30. The first end 28 can be connected to the main suture strand 14 at any desired location, for example at a distal end 18 of the main suture strand 14 or at a central portion of the main strand 14, in a variety of ways, as discussed above. The suture arms 22 can be fixedly attached to the main suture strand 14 or can be attached in a manner so as to allow the suture arms 22 to translate along a length of the main suture strand 14. The first end 28 of the suture arms 22 can alternatively include a feature, such as a loop, configured to connect the suture arm 22 to the main suture strand 14. As shown in FIG. 1, all of the suture arms 22 can be connected at a single location on the main suture strand 14. In this embodiment, the suture arms 22 are all of equal length and thus each suture arm 22 will apply approximately the same force to the corresponding suture anchor elements 24 when a load is applied to the main suture strand 14. Alternatively, the suture arms can be attached to the main suture strand 14 at varying locations. For example, each suture arm can have a different length and be attached at a location on the main suture strand that is offset by a length that is nominally equivalent to the difference in length between the suture arms. The shortest suture arm can be attached at the most distal location on the main suture strand and the longest suture arm can be attached the most proximal location on the main suture strand. Importantly, in this varied configuration, the suture arms 22 still apply approximately the same force to each suture anchor element when a load is applied to the main suture strand.

As will be described in more detail below, the suture arms 22 can be so dimensioned as to allow the suture anchor elements 24 to self-assemble in a substantially coplanar manner adjacent a surface 26 of the bone 12, as shown in FIGS. 1 and 3, when tension is applied thereto. In some embodiments, each suture arm 22 can be capable of withstanding an equal portion of the tension applied to the main suture strand 14. For example, in FIG. 1, each suture arm 22 can be capable of supporting approximately one-third of the tension applied to the main suture strand 14. To achieve this, the suture arms can be any thickness suitable for tensioning, for example in the range of about #5-0 and #5 USP size designations, and more particularly about #0. Additionally, the suture arms 22 can be any length suitable to allow proper tensioning of the suture anchor elements 24 as described herein, for example in the range of about 3 mm and 20 mm, and more particularly about 7 mm. The suture arms 22 can be formed of any known suture material, including resorbable, non-resorbable, and/or combinations thereof. Exemplary suture arm materials include for example, catgut, polyglycolide, and polydioxanone, such as EthiBond® available from Ethicon, Inc. and ORTHOCORD® High Strength Orthopaedic Suture available from DePuy Mitek, Inc. Moreover, the suture arms 22 can be a monofilament or braided.

The second end 30 of each of the suture arms 22 can be connected to a suture anchor element 24 in any manner suitable to enable secure assembly and to allow a load applied to the suture arm 22 to be transferred to the suture anchor elements 24. For example, as shown in FIG. 2A, the second end 30 can pass through a bore 34 in the suture anchor element 24 and another feature, such as a knot or a ball end 32, can be utilized to ensure that the suture anchor element 24 does not slide off of the suture arm 22. In another embodiment, as shown in FIG. 2B, the suture anchor element 24" includes a feature that enables the suture arm to be attached thereto. For example, the suture anchor element 24" can have an opening (e.g., a split along a radial plane of the suture anchor element) such that there is a gap G between a first and second portion 40, 42 of the suture anchor element 24". The gap or opening can be configured to receive a suture arm, and the suture anchor element can be configured to be deformable so that the suture anchor element can be secured to the suture arm. Although FIG. 2B illustrates a wedge-shaped gap G, one skilled in the art will appreciate that the gap G can be of virtually any shape or size.

Alternatively, as depicted in FIG. 3, the second end 30 can be attached or connected to a feature 36 on an end of the suture anchor element 24'. For example, the second end 30 can be attached directly to the feature 36, which can be virtually any feature that allows for the attachment of the suture arm (e.g., a thru-hole or cleat-like projection). The suture arm can be attached by any suitable means, such as those described above.

The suture anchor assembly can have a plurality of suture anchor elements 24, and therefore can have a plurality of suture arms 22. For example, a suture anchor assembly 10 should have more than one suture anchor element 24, but can have any number of suture anchor elements 24. For example, between 2 and 5 suture anchor elements will allow for sufficient tensioning between the suture anchor elements to prevent any one individual element from entering the opening formed through the adjacent bone, thus providing secure attachment of soft tissue. As shown in FIG. 1, the suture anchor assembly 10 has 3 suture anchor elements 24.

The suture anchor elements can have any desired geometric shape, and each element of an assembly can be of the same or different shape. For example, FIGS. 1 and 2 depict a substantially spherical suture anchor elements 24. The suture anchor elements 24 can be dimensioned such that the outer diameter OD of the element 24 is smaller than the diameter of the opening 20 in the bone 12 such that the suture anchor element can be deployed through the opening 20. But, the diameter of the suture anchor elements 24 should be large enough that a plurality of the elements 24, when tensioned so as to be adjacent to one another in a deployed suture anchor element assembly, will not pass through the opening 20 once deployed. In some embodiments the plurality of suture anchor elements 24 have substantially equivalent outer diameters, but in other embodiments the outer diameters of the suture anchor elements 24 can vary. One skilled in the art will appreciate that the size of the suture anchor elements will depend on a number of factors, including the intended application. However, in one embodiment the suture anchor elements can have an outer diameter OD in a range of about 1 mm to 10 mm, and more particularly about 3 mm.

In other embodiments, the suture anchor elements can have non-spherical geometries that fit together in a specific way when in the deployed configuration. For example, FIG. 3 depicts a substantially conical suture anchor element 24'. The substantially conical suture anchor can have a pointed proximal end 24'$p$ and a substantially spherical distal end 24'$d$, such that the substantially conical suture element 24' has a shape comprising a right circular cone attached to a hemisphere of identical diameter. In this embodiment, the suture anchor elements 24' can be dimensioned such that the outer diameter OD of the spherical distal end 24'$d$ is smaller than the diameter of the opening 20 in the bone 12 such that the suture anchor element can be deployed through the opening 20. But, the diameter of the suture anchor elements 24' should be large enough that a plurality of the elements 24', when tensioned so as to be adjacent to one another, will not pass through the opening 20 once deployed. Furthermore, as shown, the proximal end 24'$p$ can be dimensioned such that when aligned in the deployed configuration, portions of the proximal end 24'$p$ can extend into the opening 20. Alternatively, it will be appreciated that the proximal end can be the larger dimensioned end—that is, essentially reversing the orientation of the suture anchor element 24' shown in FIG. 3.

Figure 4:
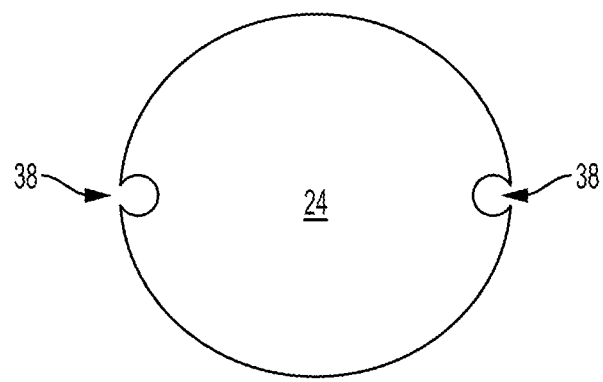
FIG. 4 is a cross-sectional view of an embodiment of a suture anchor element.
Figure 8C:
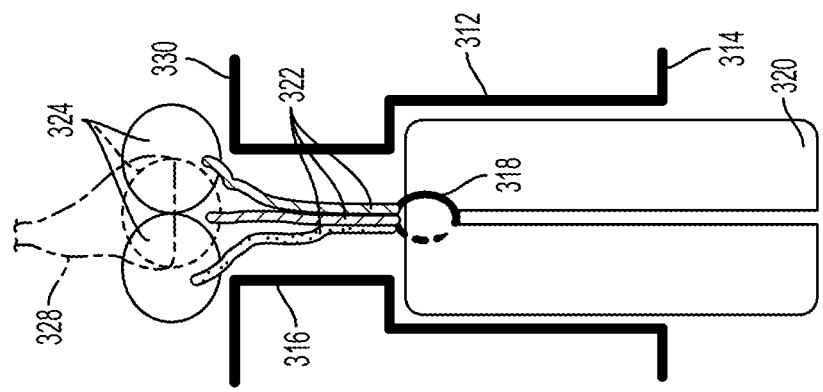
FIGS. 8A-8C sequentially illustrate an embodiment of a suture anchor assembly in an anterior cruciate ligament reconstruction application.
Figure 8B:
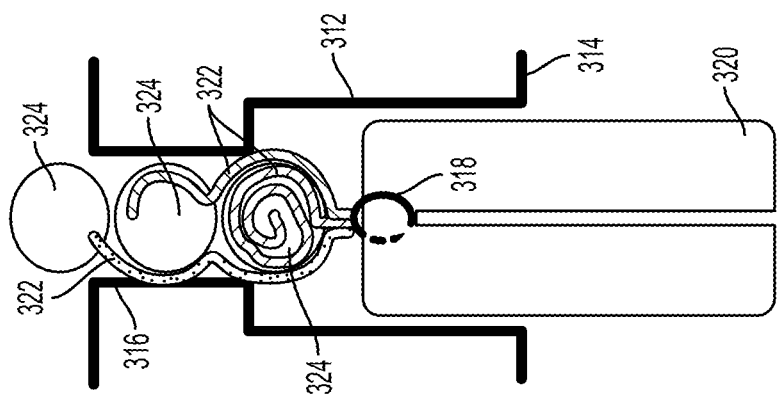
Figure 8A:
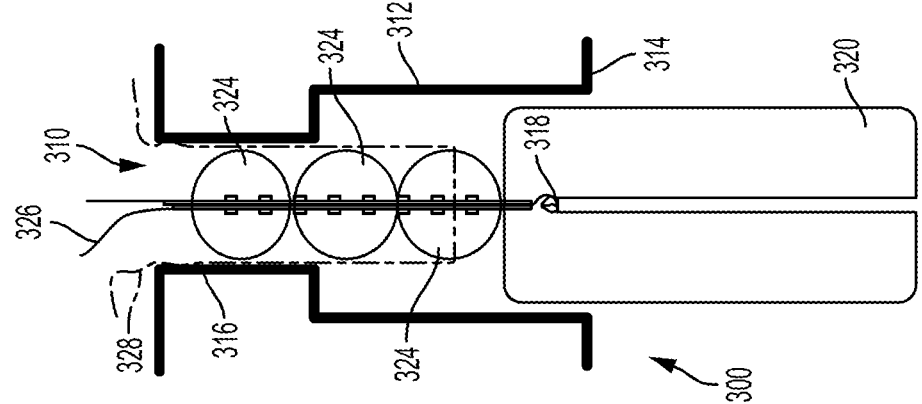

Additionally, the suture anchor elements can have a substantially smooth surface, or they can have a variety of surface features formed thereon. In some embodiments, regular indentations and protuberances can be formed on the suture anchor elements to aid in self-assembly of the suture anchor elements when moving from the delivery configuration to the deployed configuration, as will be discussed below. FIG. 4 depicts an embodiment of a suture anchor element 24 having one or more invaginations or grooves 38 formed thereon. The invaginations 38 can be configured to allow a suture strand to be wound around the anchor element 24. The invaginations 38 can, for example, be configured to have an insertion suture wrapped and/or looped around the suture anchor element 24, such as shown in FIGS. 8A and 8C. Suture management can optionally be used to prevent tangling in any of the suture arms 22 and main suture strand 14.

The suture anchor elements can be formed of any known biocompatible material, for example bone, metals, such as stainless steel and/or titanium alloys, and polymers, such as polyether ether ketone (PEEK), poly(lactic-co-glycolic acid) (PLGA), and polytetrafluoroethylene (PTFE), and/or ceramics. In some embodiments, materials that promote healing, such as tricalcium phosphate (TCP) or any other osteoconductive ceramic or polymer, can be used. In some embodiments the anchor can be formed of a material that will completely turn to bone as it heals. Exemplary materials can include Biocryl Rapide® available from DePuy Synthes Products, LLC.

As is mentioned above, the suture assembly 10 can be manipulated between a delivery configuration and a deployed configuration. For example, in an embodiment of the delivery configuration, each suture element 24 can be substantially aligned along a central axis and able to pass through an opening in bone, such as opening 20 shown in FIG. 1.

Figure 5:
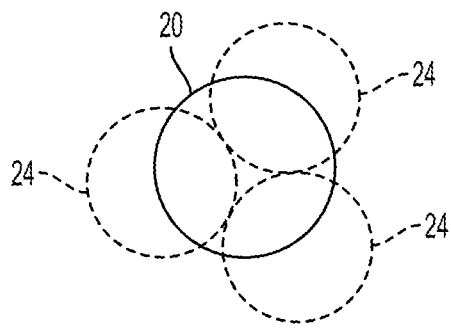
FIG. 5 is a partial top view of the suture anchor assembly of FIG. 1 in a deployed configuration.

FIGS. 1, 3, and 5 show the suture anchor assembly in a deployed configuration. In an embodiment of the deployed configuration, the suture anchor elements 24 can be oriented in a coplanar manner substantially parallel to a bone surface, such as surface 26 in FIGS. 1 and 3, and unable to pass through the opening in bone. The suture assembly 10 can be self-assembling, for example by tensioning the main suture strand, the suture elements can be rearranged into a deployed configuration in which the suture anchor elements separate and are oriented in a coplanar manner substantially parallel to the bone surface and unable to pass through the cavity. To maintain the suture anchor assembly in the deployed configuration, the suture arms 22 can be maintained at a substantially equal tension. By maintaining each suture arm 22 at a substantially equal tension, the suture anchor elements 24 will separate and self-assemble into a coplanar configuration adjacent the opening 20 that the suture anchor elements 24 were delivered through, as shown in FIG. 5. Upon deployment in this coplanar arrangement, as shown in FIG. 5, the suture anchor elements 24 form a suture anchor element assembly that cannot pass through the opening 20. That is, as any individual suture anchor element 24 is tensioned against any other individual anchor element, the assembly blocks the opening from any individual anchor element 24.

As noted above, in the deployed configuration, it is desirable to have equal or near-equal tension on the individual suture anchor elements 24 so that no single suture anchor element can re-enter the opening and thus cause the fixation to fail. A technique of ensuring secure fixation is to simply have all of the suture anchor elements 24 spaced equidistant from the main suture strand 14. This can be accomplished by having the length of each of the plurality of suture arms 22 be substantially equal. Another technique for achieving a similar, iso-tension state is to utilize a locking device (not shown) able to slide down the main suture strand 14 and onto the suture arms 22 following deployment of the suture anchor elements 24. Such a locking device can be useful in cases where the suture arms are not of the same length and/or are subject to un-equal tension. A suitable locking device, which can be any suitable shape, can be fixed upon actuation at a specific point and prevent slippage of the suture arms. One example of a locking mechanism a ring-like mechanism than can be deformed to its actuated state. In such an embodiment, the ring can be deformed or actuated by a specific instrument to lock on the suture strand in any desired location.

In use and following accepted surgical procedures, involving either open or minimally invasive surgery, an opening or cavity in a bone can be formed prior to delivering a suture anchor assembly. For example, a practitioner can use an awl, drill, and/or an inflatable balloon to create an opening 20 that has a cavity diameter that is larger than the diameter of an individual suture anchor element 24. In one embodiment, the cavity diameter can be approximately three times larger than the outer diameter OD of an individual suture anchor element 24. The opening 20 can be formed such that the suture anchor elements 24 will rest on a superficial surface of the cortex, or alternatively on a deep surface of the cortex.

Figure 6:
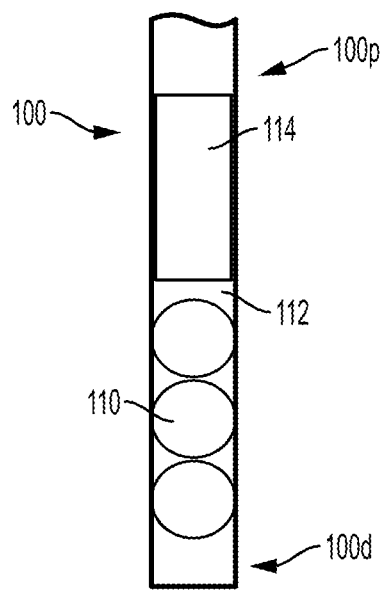
FIG. 6 is a cross-sectional view of an embodiment of an inserter tool with a suture anchor assembly disposed therein in a delivery configuration.

After formation of the opening in the bone, the suture anchor assembly can be delivered into the opening. In use, the suture anchor assembly is maintained in a delivery configuration while being delivered into the opening, as described above. The suture anchor assembly can be delivered into the opening in any manner that maintains the assembly in a delivery configuration. For example, a flexible sleeve can be included to maintain the suture anchor elements in a generally linear alignment. Alternatively, the suture anchor assembly can be delivered to the opening in the bone with an inserter tool. FIG. 6 depicts an embodiment of an inserter tool 100 having a proximal end 100*p* and a distal end 100*d*. The inserter tool 100 can include a hollow tubular member 112 that is configured to house the suture anchor assembly 110 and maintain the suture anchor assembly 110 in a delivery configuration. The inserter tool 100 can have a lumen extending from the distal end 100*d* to the proximal end 100*p* to allow portions of the suture anchor assembly 110, such as the main suture strand (not shown), to extend proximally through the inserter tool. The inserter tool 100 can also include a plunger 114, or a similar element, to selectively deploy the suture anchor assembly 110. In use, the plunger 114 can be translated distally through the hollow tubular member 112 to push the suture anchor assembly 110 out of an opening in the distal end 100*d*. When the suture anchor assembly 110 exits the inserter tool 100, the suture anchor assembly 110 is free to self-assemble to the deployed configuration. The inserter tool 100 can optionally include an indicator marking on an exterior surface of the inserter tool 100 so as to indicate when the suture anchor assembly 110 has been placed deeply enough through the opening in the bone to translate the plunger distally and deploy the suture anchor assembly 110. Once the suture anchor assembly 110 is deployed from the inserter tool 100, the main suture strand can be tensioned causing the suture anchor assembly 110 to self-assemble in the manner described above.

As noted above, the suture anchor assembly described herein is applicable to a variety of surgical procedures requiring soft tissue and/or graft attachment or reattachment.

Two exemplary applications are described below. One skilled in the art will appreciate the general surgical technique applicable to the procedure. Thus, the descriptions below emphasize differences in technique occasioned by the use of the suture anchor assembly described herein. Portions of the technique not affected by the suture anchor assembly described herein will not be described.

Rotator Cuff Repair

Figure 7:
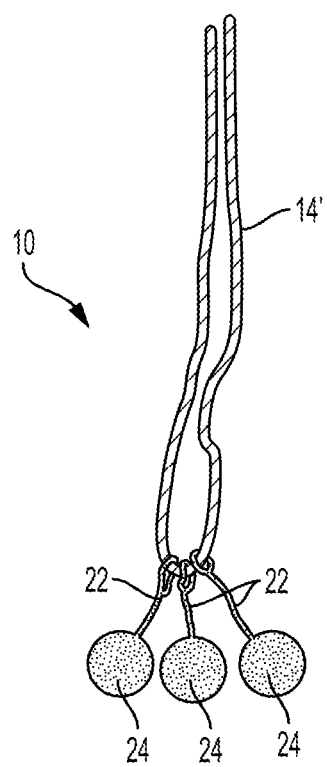
FIG. 7 is a side view of an embodiment of a suture anchor assembly for use in a rotator cuff repair application.

For rotator cuff repair, an inserter tool, much like the one described in FIG. 6, can be used with the suture anchor assembly 10 depicted in FIGS. 1-5, however, a modified main suture strand 14', as seen in FIG. 7, can be used. Specifically, since a sliding knot is typically tied in the main suture strand 14', in minimally invasive rotator cuff repair it is desirable to have two ends of the main suture strand 14' available. Additionally, as is shown in FIG. 7, the suture arms 22 are attached to the main suture strand in a manner that allows them to translate along the length of the main suture strand 14'.

During the surgical procedure, the surgeon will prepare the soft tissue and bone as described above and as is typical in rotator cuff repair procedures. An appropriately-sized opening or hole is formed in the bone and the inserter tool 100 is placed either at the mouth of the hole or slightly inside the hole. By depressing the plunger, the surgeon will deploy the suture anchor elements 24. Then, the inserter tool 100 can be removed and the main suture strand 14' passed through soft tissue and tied using techniques known in the art of rotator cuff repair. Depending on the density of the bone, it may be necessary to remove some amount of cancellous bone so that the suture anchor elements have adequate space to move and come to a planar resting point just underneath the cortex.

ACL Reconstruction

An additional use of the suture anchor assemblies disclosed herein is for anterior cruciate ligament (ACL) reconstruction. In ACL reconstruction femoral fixation is a common method of reconstructing the damaged ACL. FIGS. 8A-8C depict a suture anchor assembly 310 in various stages of use in a femoral fixation procedure.

As part of the surgical technique, an opening in the femur 300 is formed to create a femoral socket 312 using known surgical techniques. For example, an appropriately sized femoral socket 312 can be created by first drilling a beath pin through a medial surface 314 of the femur at an appropriate entry point and angle to create an opening or cavity in the femur. The cavity can then be overdrilled to create a passing channel 316 for the suture anchor assembly 310 that passes through a lateral cortex 318 of the femur. Next, the femoral socket 312 of appropriate length is formed along the passing channel 314 by overdrilling the socket.

Once the femoral socket 312 is formed, the graft 320 can be attached to the suture anchor assembly 310 and delivered into the femoral socket 312. The graft 320 can be attached to the suture anchor assembly 310 by any means suitable, for example by looping the main suture strand 318 around the graft 320. As shown in FIG. 8A, an exemplary suture anchor assembly 310 can have three spherical suture anchor elements 324 and a graft seating suture 326 that is threaded through the passing channel 316, for example by passing the graft seating suture 326 through the suture anchor elements 324. The assembly can further include an insertion suture 328 that is configured to pass or deliver the suture anchor elements 324 through the passing channel 316. For example, the insertion suture 328 can be threaded through or around the distal most suture anchor element 324, as shown in FIG. 8A. As shown in FIG. 8B, the suture anchor assembly 310 can employ a suture management system, that is, the suture arms 322 can be wrapped around the suture anchor elements 324 in a manner that will aid in keeping linear alignment during delivery of the suture anchor assembly 310 and that will unravel and expand when the suture anchor assembly is in a deployed configuration.

As shown in FIG. 8C, once the graft 320 is sufficiently seated in the femoral socket 312, the graft seating suture 326 can be removed by pulling one end of the graft seating suture 326. The insertion suture 328 can then be pulled in a proximal direction (an upward direction in FIG. 8C), so as to advance the suture anchor elements through the passing channel 316. Once the distal most suture anchor element 324 has passed through the passing channel 316, the insertion suture can be removed by pulling one end of the insertion suture 328. In this deployed configuration, the suture anchor elements 324 are free to self-assemble into the coplanar arrangement against the lateral cortex 330 as shown in FIG. 8C.

A person skilled in the art will appreciate that the present disclosure can have application in any application requiring the fixation of a graft or tissue to bone. For example, the subject matter of this disclosure can be used in fixation of the proximal biceps tendon to the humeral shaft in the subpectoral location.

The suture anchor assemblies and inserter tools described herein can be included in surgical kits. For example, a surgical kit for repairing tendon or ligament can include a suture anchor assembly, such as that depicted in FIGS. 1-4 and 7. That is, the suture anchor assembly can include a main suture strand, a plurality of suture arms, each having at least a first end attached to the main suture strand, and a plurality of suture anchor elements, each connected to one of the suture arms, wherein the suture anchor assembly has a delivery configuration in which each suture element is substantially aligned along a central axis and able to pass through an opening in bone and a deployed configuration in which the suture anchor elements are oriented in a coplanar manner substantially parallel to a bone surface and unable to pass through the opening in bone. The surgical kit can further include an inserter tool such as that described in FIG. 6. The inserter tool can be configured to selectively maintain the suture anchor assembly in the delivery configuration until deployment. Further, the surgical kit can have an inserter tool with a suture anchor assembly preloaded into the inserter tool. The surgical kit can include additional items, such as a plurality of suture anchor assemblies, additional suture lengths, tissue preparation tools such as a beath pin, and any other element that is typically used in suture anchor applications.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical repair method, comprising:
    forming a cavity within bone, the cavity having a cavity diameter;
    delivering into the cavity a self-assembling suture anchor assembly in a delivery configuration, the suture anchor assembly having a main suture strand, and a plurality of suture elements each connected to the main suture strand by a respective separate suture arm;
    deploying the suture anchor assembly by tensioning the main suture strand such that the suture elements are rearranged into a deployed configuration in which the suture anchor elements are oriented in a coplanar manner substantially parallel to the bone surface and unable to pass through the cavity; and
    securing a graft or soft tissue connected to the suture anchor assembly to bone.

2. The method of claim 1, wherein during the delivery step the suture anchor elements are disposed within an inserter tool and the inserter tool is disposed through at least a portion of the cavity.

3. The method of claim 1, wherein the graft or soft tissue is attached to the main suture strand.

4. The method of claim 1, wherein each suture arm is of a substantially equal length.

5. The method of claim 1, wherein each suture anchor element is spaced substantially the same distance from a distal end of the main suture stand.

6. The method of claim 1, wherein each suture arm is attached to the main suture strand at varying locations.

7. The method of claim 1, wherein each suture anchor element has a shape that is one of substantially conical and substantially spherical.

8. The method of claim 7, wherein the at least one suture anchor element has an opening formed therein, the opening being configured to receive the respective one of the suture arms and being configured to be closeable so that the suture anchor element can be secured to the respective one of the suture arms.

9. The method of claim 1, wherein each suture anchor element has a bore extending therethrough, the bore sized and configured to accept respective one of the suture arms in a clearance fit.

10. The method of claim 1, wherein each suture anchor element has one or more surface features formed thereon, the one or more surface features configured to enable joinder of adjacent suture anchor elements to one another.

11. The method of claim 1, wherein each suture anchor element has at least one invagination surface feature.

12. The method of claim 1, wherein the suture anchor elements are formed of a material selected from the group consisting of bone, metal, polymers, and ceramics.

13. The method of claim 1, wherein the suture anchor elements are formed of an osteoconductive material or a bioresorbable material.

14. The method of claim 1, further comprising a graft material affixed to the main suture strand.

15. The method of claim 1, wherein the suture anchor assembly comprises three suture arms and three suture anchor elements.

16. The method of claim 1, wherein each suture anchor element has at least one groove surface feature thereon configured to receive the second terminal end of the respective one of the suture arms and secure the respective one of the suture arms to the respective suture anchor element.

17. The method of claim 1, wherein each suture anchor element is fixedly connected to only the second terminal end of the respective one of the suture arms.

18. A surgical repair method, comprising:
    forming a cavity within bone;
    inserting distally into the cavity a self-assembling suture anchor assembly in a first position, the suture anchor assembly having
        a main suture strand, and
        a plurality of secondary suture strands each attached to the main suture strand at respective first terminal ends thereof and to respective suture anchor elements at respective second terminal ends thereof; and
    transitioning the suture anchor assembly from the first position to a second position by retracting proximally the main suture strand to tension the plurality of secondary suture strands and prevent passage of the plurality of suture anchor elements proximally out of the cavity.

19. The method of claim 18, inserting the suture anchor assembly further comprises inserting an inserter tool having a hollow tubular member configured to house the suture anchor assembly and a plunger configured to selectively deploy the suture anchor assembly.

20. The method of claim 18, further comprising securing a graft or soft tissue connected to the suture anchor assembly to bone when the suture anchor assembly is in the second position.

* * * * *